United States Patent
Sodi et al.

[11] Patent Number: 5,547,566
[45] Date of Patent: Aug. 20, 1996

[54] DEVICE FOR DETECTING AND MEASURING CONTINUOUSLY SURFACTANT SUBSTANCES IN WATER

[76] Inventors: Paolo Sodi, Via Cesare Balbo No.31, 50047 Prato; Roberto Sodi, Via Ugo Foscolo No.5, 50018 Scandicci, Firenze both of Italy

[21] Appl. No.: 338,023

[22] Filed: Nov. 10, 1994

[30] Foreign Application Priority Data

Nov. 11, 1993 [IT] Italy ................................ FI93A0228

[51] Int. Cl.⁶ .............................. B01D 17/12; G01N 13/02
[52] U.S. Cl. .......................... 210/87; 73/64.48; 73/64.52; 210/175; 422/82.05
[58] Field of Search ................. 210/87, 94, 109, 210/181, 416.1, 175, 348; 422/68.1, 81, 82, 82.05, 101, 103, 106, 109, 110, 116; 436/52, 53, 54, 177, 180; 73/64.48, 64.52, 64.51

[56] References Cited

U.S. PATENT DOCUMENTS

| | | | |
|---|---|---|---|
| 2,473,553 | 6/1949 | Stokes | 73/64.52 |
| 3,030,192 | 4/1962 | Schneider | 422/81 |
| 3,189,533 | 6/1965 | Anscherlik | 422/81 |
| 3,259,462 | 7/1966 | Anscherlik | 422/81 |
| 3,436,188 | 4/1969 | Boyd et al. | 422/81 |
| 3,627,494 | 12/1971 | Fahnrich | 422/81 |
| 3,913,385 | 10/1975 | Jobe | 73/64.52 |
| 4,196,615 | 4/1980 | Davis | 73/64.52 |
| 4,725,407 | 2/1988 | Usui et al. | 436/53 |
| 5,167,144 | 12/1992 | Schneider | 73/64.52 |
| 5,218,841 | 6/1993 | Hool | 73/64.52 |

FOREIGN PATENT DOCUMENTS 1147556  4/1969  United Kingdom ............... 422/82

Primary Examiner—Joseph W. Drodge
Attorney, Agent, or Firm—McGlew And Tuttle, P.C.

[57] ABSTRACT

Gaseous bubbles are made to rise in two respective measuring columns (30,20) for purified reference water and for the water to be examined, which columns are supplied with descending currents and drained by respective ascending discharge columns (34,24) and overflows (36,26); the bubbles are measured with a konimeter on the rising sections, and the difference in rising times in the two columns is calculated, in order to determine the extent of the presence of surfactants.

20 Claims, 2 Drawing Sheets

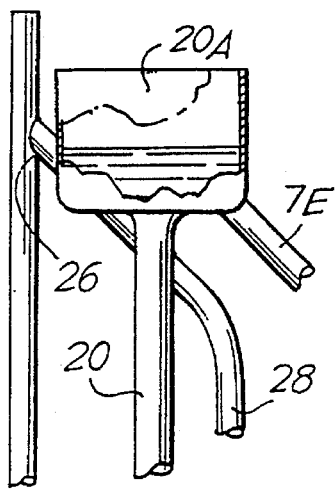
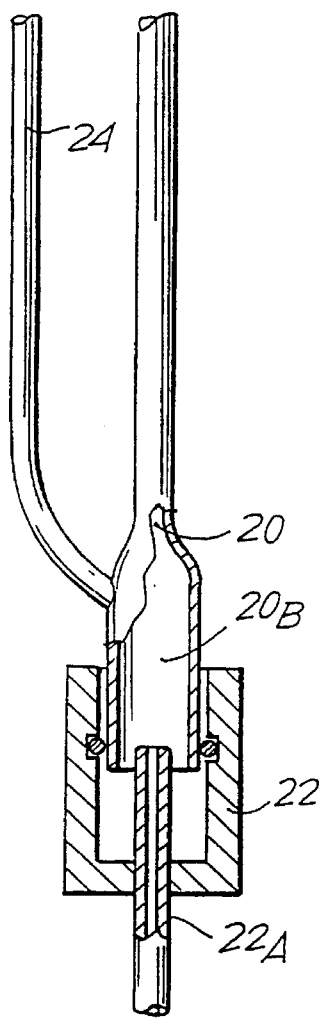
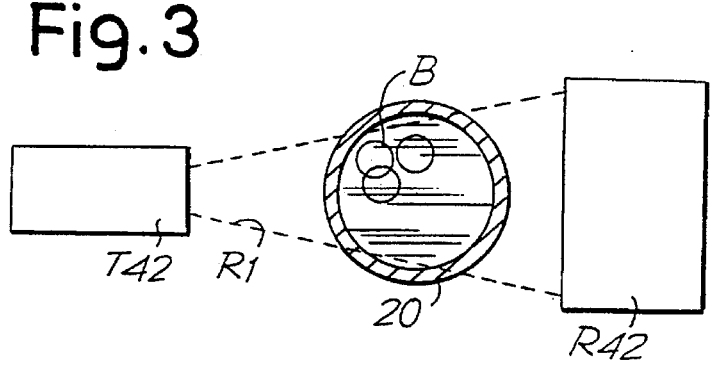
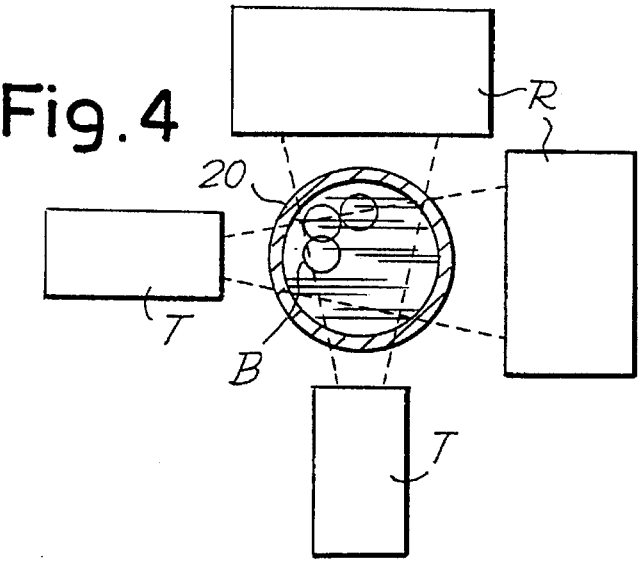
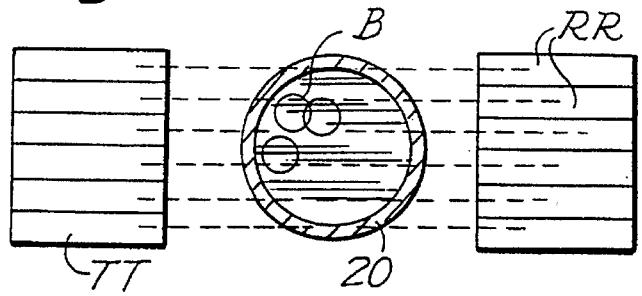

DEVICE FOR DETECTING AND MEASURING CONTINUOUSLY SURFACTANT SUBSTANCES IN WATER

FIELD OF THE INVENTION

The present invention relates to a device for measuring the concentration of surfactant substances, in particular to measuring the concentration by measuring the speed of bubbles through a test solution and a reference solution.

A gaseous bubble in water tends to rise to the surface owing to fluid pressure; in pure water, its speed of rising depends on various factors, because of the complex dynamics which occur on the surface of the bubble. As the bubble rises, its outer surface is subjected to stress caused by the forces of sliding friction of the external fluid. The outer layer of the bubble transmits part of the motion of the external fluid to the gas contained in the bubble, inducing motion in the gas; this phenomenon means that sliding friction during rising is considerably reduced, and the bubble rises in pure water at a speed which is far higher than would be the case if it were a body of the same dimensions and density, but with a rigid surface structure characteristic of solids.

BACKGROUND OF THE INVENTION

If the gaseous bubble moves in water which contains surfactant substances, other phenomena, which change its speed considerably, intervene. Owing to their structural features, these substances have the property of distributing themselves spontaneously at the water/air interphase in concentrations which are far higher than those which occur in the mass of the water, giving rise to the formation of an adsorption film which is generally monomolecular (i.e. of the thickness of one molecule of the substance adsorbed). In the case of rising gaseous bubbles, adsorption of a surfactant substance on the surface of the bubble gives rise to a film which, depending on the mass concentration of the rising path and the surface activity of the product, enriches the surface of the bubble of surfactant molecules such as to confer rigidity on the surface of the bubble. The transmission of quantities of motion to the gases (or most commonly to the fluid contained in the bubble) is prevented in this case, and friction on the surface of the bubble increases as the surface concentration increases, until that of a typical solid structure is obtained. In other words, by adsorbing the surfactant material on its surface, the bubble acquires the same features as a solid body, and therefore follows Stokes' law, which governs the motion of a solid sphere which is left free to move in a fluid of a different density.

By measuring the decrease in speed of rising of a bubble in aqueous means, the above-described phenomena as a whole permits detection of the presence of surfactants, even in the form of traces. In fact, the phenomenon of adsorption can increase up to thousands of times the difference of concentration between the surfactant molecules distributed on the water/air interphase, compared with that of the same molecules in the mass of aqueous solution. Consequently, even for small concentrations of mass of surfactant substance, considerable changes occur in the surface features of the bubble, with a final increase in rigidity of the interphase surface. Quantitatively, this phenomenon can be evaluated on the basis of the surface viscoelasticity of the adsorption film.

Adsorption is not an instantaneous phenomenon, and in order to achieve the excess of surface concentration in thermodynamic balance with the concentration of the surfactant in the mass of the water, the bubble requires a specific time equivalent to a specific path of rising for a specific concentration. The speed of rising of the bubbles also depends greatly on the dimensions of the latter; for bubbles of 2–3 mm in diameter this is approximately 30 cm per second in pure water at ambient temperature. For bubbles of this diameter, a path of several meters is required before the conditions of saturation of the respective adsorption surface are obtained. This last aspect is very important because the phenomenon of adsorption, and still more the corresponding surface viscoelastic properties, reach constant values upon full saturation of the adsorption surface. In practice, the linearity of the aforementioned phenomena is also achieved only for surface concentrations of the bubble; for the first 50 cm of path, it is virtually linear even for limit mass concentrations of 1 mg/l of surfactant, with surface activity comparable to those commonly used as detergents.

In addition to detecting the surfactants present, it is thus also possible to obtain information on their concentration. In any case, when an empirical calibration curve is plotted with a surfactant which has surface expansion properties of the same type as those of the aqueous solutions being examined, information can be obtained concerning the mass concentration of higher concentrations as well.

SUMMARY AND OBJECTS OF THE INVENTION

The object of the invention is to provide a device for obtaining reliable measurement results, even with a small-sized device, and which is free from significant influences by variable external factors. This and other objects and advantages will become apparent from the following text.

The device in question, for measuring the quantity of surfactant substances in water by calculating the speed of rising of gaseous bubbles in a water column to be examined, substantially comprises in association: two structures which form respective measuring columns for pure reference water and for the water to be examined, with respective systems for gas bubble generating; means for supplying the two types of water from the top into the two columns and for creating descending currents therein; discharge column which extend from the lower area of the measuring columns and the tops of which end in an overflow; in said discharge columns rising currents are formed downstream of the measuring columns, in order to ensure that the level in the two measuring columns remains constant.

The device comprises a circuit for supplying water to be examined, and this circuit is divided into a first circuit which supplies the measuring column for the water to be examined, and a second circuit which supplies pure water, containing a purification filter; each circuit contains its own pump which has the same features for both circuits, and a heat exchanger is provided which regularizes the temperatures of the fluid in transit in said first and second circuits immediately before supply to the respective measuring columns.

Each of the two measuring columns has on its upper part an open chamber with a relatively wide cross-section in order to constitute a stabilizing chamber for the level of the water in the columns, in relation to the pulses of the respective pumps.

The measuring technique therefore consists of measuring the difference between the speed of rising of similar gaseous bubbles, which rise respectively in the water fluid column in question, and in the fluid column which has the same physical conditions and dimensions, using the same water but without surfactants, owing to removal of the latter by activated carbon or another filtering system. The columns (which are made of pyrex glass) have the same height and cross-section. Water is made to flow in the columns from the top, in order to be able to remove the water from the columns and use the device for continuous measuring. The flow of water (2–3 liters/hour) is maintained strictly the same, using the same pumps and other factors which are the same in the two circuits, in order to avoid introducing arbitrary differences in the speed of rising of the bubbles. The gaseous bubbles have the same volume, since they are generated by means of capillary units, the ends of which are exactly the same. The number of bubbles in the unit of time (for example approximately every two seconds) is regulated by microvalves which control distribution of the gas. Nitrogen is advantageously used as the gas; this product is sufficiently pure to avoid affecting the measurements, even over long periods of time. Particular care is obviously taken with the gas ducts, for the same purposes.

The activated carbon cartridge, or other filtering system, plays a fundamental part, since it must ensure total compliance with the limits of sensitivity of the device (approximately 0.001 mg/l of dodecylbenzene sulfonate) throughout the entire measuring period. The duration is associated with the concentrations of surfactant in the respective volumes of water treated. A meter at the device intake can constitute a useful indicator; alternatively, a system for measuring the time of use of the filter can be adopted, by means of the computer with which the instrument will be equipped.

The speed of rising of the bubbles relates to the same distances, and is clearly defined in the two columns; thus, for the purposes of comparative measurements, it is sufficient to measure the difference in the times of rising which constitute the effective parameter of the device.

The data can be suitably processed. For example the digitized signal is stored in a small computer or control means, which, by means of appropriate software, calculates the mean value of a specific number of differential measurements, and then compares them with the calibration curve in order to give the concentrations of surfactant directly.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings;

FIG. 2 is a schematic detail of operation of the device; and

FIGS. 3, 4 and 5 show diagrams of possible sensors for detecting transit of the bubbles.

DETAILED DESCRIPTION OF THE PREFERRED EMBODIMENT

Figure 1:
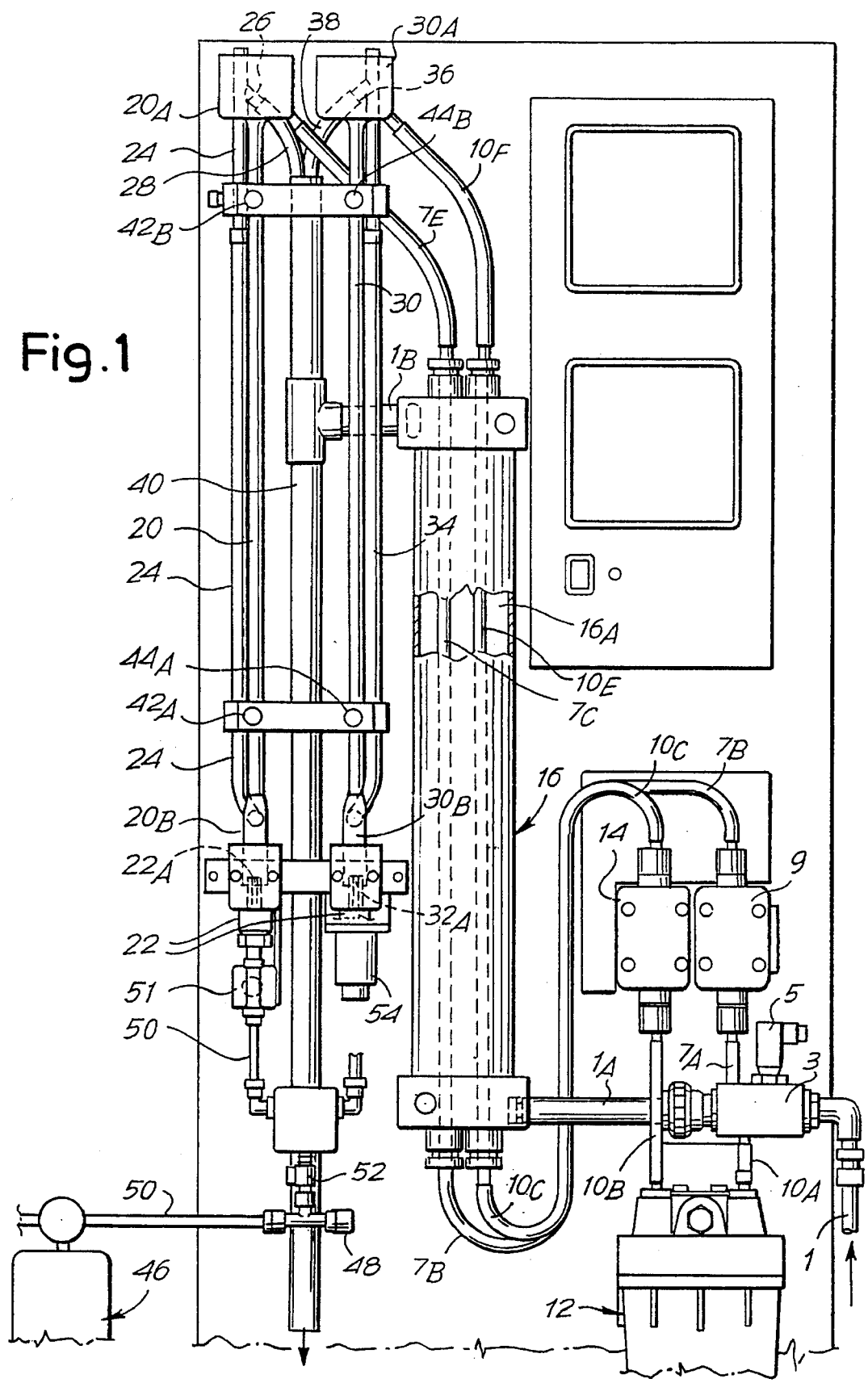
FIG. 1 is a general schematic view of the device.

In the illustration in the appended drawings, 1 indicates the supply of water to be examined, which reaches an input manifold 3 provided with a pressure switch 5. From the manifold 3 there extends a first fluid supply circuit or means which comprises ducts 7A, 7B and a circulation pump 9, for example a diaphragm pump, in order to supply said first circuit with the water to be examined. From said manifold 3 there also extends a second fluid supply circuit or means 10A, 10B, 10C, in which there is inserted a filter 12, for example an activated carbon filter, as well as a pump 14 downstream of the filter 12, which is similar to the pump 9 for circulation of pure water, which is purified by means of the filter 12, which in particular can eliminate the presence of surfactants. The two circuits 7A, 7B and 10A, 10B, 10C extend to a heat exchanger 16 which comprises a chamber 16A intersected by two ducts 7C and 10E which constitute extensions of the two circuits 7A, 7B and 10A, 10B, 10C; the chamber 16A is filled by a fluid at a regular temperature, which regularizes the temperature of the water circulating slowly through the two ducts 7C and 10E, owing to the low capacity of the two pumps 9 and 14; this chamber 16A can in fact be intersected by an extension 1A of the supply duct 1 downstream of the manifold 3, leading to a discharge 1B, with a rising current in the heat exchanger 16, and thus with a current similar to that of transit in the two ducts 7C and 10E. The two ducts 7C and 10E are made of a material which has a satisfactory heat exchange capacity, for example glass.

The circuit 7A, 7B, 7C, 7E of the water to be examined (see also FIG. 2) extends to a beaker 20A which is at the upper end of the measuring column 20 for the water to be examined; the beaker 20A is open to the atmosphere, and has a cross-section which is sufficiently wide to ensure that the pulses of the pump 9 do not make the level in the beaker 20A vary substantially, which level is stabilized by an overflow described hereinafter. The measuring column 20 for the water to be examined has at its enlarged lower end 20B a connection body 22 for a gas distributor, for example for nitrogen bubbles, this distributor being indicated by 22A. From the end 20B there extends, with a deviation relative to the axis of the measuring column 20, a discharge column 24, which is open as in the case of the beaker 20A, and which has an overflow 26 for discharge to a discharge duct 28. Similarly the circuit 10A, 10B, 10C, 10E, 10F extends to a beaker 30A of a measuring column 30 for the pure water, i.e. for the water purified by the filter 12; on its lower end 30B the column 30 has a gas bubble distributor 32A, and to said end a discharge column 34 is connected which is similar to 24 and also has an overflow 36 leading to a discharge duct 38; the two discharge ducts 28 and 38 extend to a drainage column 40, to which the discharge 1B can also be connected. The beakers 20A, 30A and the overflows 26, 36 form a flow stabilization means for maintaining the flow of fluid in the columns substantially constant.

The position of the two overflows 26 and 36 is particularly important for establishing the height of the water column present in each of the measuring columns; in fact this height considerably affects the times of rising, owing to compression caused by the hydraulic load, which takes place on the bubble at the moment of its formation in the capillary unit, and thus also to variation of the volume of the bubble as it rises, with a consequent variation of speed. In order to prevent this from occurring, the height of the two discharge levels is calibrated, in order to eliminate all errors of difference in level caused by processing tolerances, lack of levelness of the ground where the device is installed, errors of verticality and the like. In practice, the position of the levels can be adjusted by making at least one of the columns 24 or 34 or at least one of the complexes 20, 24 or 30, 34 slide axially by friction relative to the other.

Said two distributors 22A and 32A must be exactly the same; in practice this can be obtained by etching and breaking into two parts a capillary unit (made of glass or the like), which parts are used as distributor nozzles. FIG. 2 shows the distributor nozzle 22A inserted in the body 22, inside the cavity of which the lower end 20B of the column 20 is sealed.

In association with each of the two columns 20 and 30 there are provided two or more detectors, such as optical sensors, photocell-type optical sensors or other types of sensors, including those of the electrical type. These detectors are indicated by 42A, 42B and 44A and 44B respectively, and are spaced from one another on the respective column, and similarly on the two columns. These detectors can check passage of the gas bubbles, which can be nitrogen, and are combined with a suitable opto-electronic and data processing interface system, in order to indicate the speeds of rising of the respective bubbles, and thus the times of passage between one detector and the next successively reached by the individual bubbles, or in other words the values of concentration of the surfactants.

The sensors which detect passage of the bubbles such as 42A, 42B and 44A, 44B, can be opto-electronic transducers of one of the types shown in FIGS. 3, 4 or 5. In FIG. 3, a single transmitter T42 emits a beam R1 which is wide enough to cover all the cross-section of the column, and is captured by a receiver R42 with a substantial surface width; in FIG. 4 there are provided two units, T for transmission and R for reception, similar to T42 and R42, which are disposed at right angles to one another; in FIG. 5, a row of transmitters TT can interact with a row of receivers RR. In all cases, a feature of the sensors is that they are also sensitive to the passage of bubbles B which are very close to the walls. In addition, the transmitters are advantageously activated at a high frequency in order to obtain a good level of discrimination by the receiver, with respect to ambient light.

The two gaseous bubble distributors 22A and 32A are supplied by a source indicated by 46, for example of nitrogen, which is controlled by means of a pressure switch 48, and includes on the double circuit a supply unit 50 which has micrometric capacity regulators 51 and a solenoid valve 52, which is normally closed and is opened at the start of operation. Solenoid valves 54 (only one of which is shown on the drawing) are provided at the base of the two column 20 and 30; these solenoid valves are normally open and are closed when operation begins, in order to allow the water coles to be emptied when required.

The two pumps 9 and 14, which supply the two measuring columns, have a structure which is absolutely identical, and they are driven by means of a single geared motor or motors which are perfectly synchronized. This guarantees that the capacities, and thus the speeds of descent in the two column, are the same. The factor of speed of descent of the water in the two columns is essential for operation of the device, since if the water descends faster in one column than in the other, the times of rising of the bubbles change, and the measurement is incorrect, since it is determined differentially between the times of the two columns.

In order to ensure that the temperature conditions are the same in the two columns, the equalizer 16 is provided, which can also function in a manner other than that described, in order to establish a relatively high temperature difference in the flows for the two columns.

For the purpose of satisfactory control of the device, the solenoids which empty the columns and control the gas are provided. The two solenoid valves 54 are used to control the state of the water inside the columns, and if the device is switched off or gas is lacking (detected by the pressure switch 48), the solenoid valves 54 (which are normally open) open and empty the water from the measuring columns 20 and 30; without these valves, the lack of gas outlet would mean that the capillary units could fill with water and their bubble-forming performance could be altered, in addition to potential oxidation of the micrometric regulator 51 for the gas flow; the solenoid valves 54 are advantageously of the type which is normally open, so that if the power is switched off, the emptying process takes place automatically. The solenoid valve 52 for the gas also functions on the same principle, but conversely, since it is of the type which is normally closed, and thus if the power is off, it protects against unnecessary emptying of the gas cylinder.

The device comprises software systems for full control of the individual parts (gas pressure switch, gas solenoid valve, water pressure switch, water solenoid valves and the four photocells); a computerized system of this type measures the times of rising of the bubbles in the two columns and calculates repeatedly the mean of the last $n$ bubbles (for example the last 200 bubbles), each time discarding the previous values, and processes the data for comparison, until values are provided which can be expressed in the units required.

The materials used for the device are mainly glass, so-called Teflon, silicone and/or other materials which cannot retain or emit surfactants, or retain or discard various concentrates.

The device ensures perfect regularity of operation, and uniformity of conditions in the two measuring columns, concerning both temperatures and capacities, such as to obtain particularly reliable measurements. The countercurrent downward path of the relatively slow flow of water in the measuring columns, which is thus in a direction opposite the rising direction of the bubbles, enables the length of the individual columns to be limited, with the same result. It is thus clear that according to the arrangements indicated, a device is obtained which, even with relatively limited dimensions, enables substantial accuracy of measurement, and thus substantial reliability, to be obtained.

It is understood that the drawing only gives an embodiment provided as a practical demonstration of the invention, the forms and arrangements of which can be varied without departing from the concept underlying the invention. The existence of any reference numbers in the attached claims is intended to facilitate reading of the claims with reference to the description and the drawing, and does not limit the scope of protection represented by the claims.

We claim:

1. A device for measuring a surfactant substance, the device comprising:

a first measuring column for containing a reference fluid;

a second measuring column for containing a test fluid;

a first bubble means connected to said first measuring column and for generating bubbles in said first measuring column;

a second bubble means connected to said second measuring column and for generating bubbles in said second measuring column;

flow stabilization means connected to said first and second measuring columns to create separate flows through said first and second measuring columns, and to maintain the flows in said first and second measuring columns substantially constant and similar, said flows being substantially opposite to a buoyancy direction of the bubbles;

fluid supply means connected to said first and second measuring columns and for supplying the reference and test fluids to respective said first and second measuring columns;

filter means positioned in said fluid supply means and for filtering the test fluid to form the reference fluid;

heat exchanger means positioned in said fluid supply means and for equalizing temperatures of the reference fluid and the test fluid.

2. The device as claimed in claim 1, wherein;

a portion of said first and second discharge column means are each adjustable for leveling thereof.

3. The device as claimed in claim 1, wherein;

said first and second bubble means are formed from two sections of a single capillary tube, divided so as to be equal.

4. The device as claimed in claim 1, further comprising:

automatic solenoid means for discharging fluid from the first and second measuring columns and for closing the first and second bubble means each time operation of the device is interrupted.

5. The device as claimed in claim 1, further comprising:

computerization means to determine a mean of a time of passage of a last n bubbles generated, n being set at will.

6. A device in accordance with claim 1, wherein:

said flow stabilization means includes first discharge column means for maintaining a level of fluid in said first measuring column substantially constant, said first discharge column means being positioned and connected to a downstream end of said first measuring column to cause a direction of flow in said first discharge column means to be substantially opposite to a direction of flow in said first measurement column, said flow stabilization means also includes a second discharge column means for maintaining a level of fluid in said second measuring column substantially constant, said second discharge column means being positioned and connected to a downstream end of said second measuring column to cause a direction of flow in said second discharge column means to be substantially opposite to a direction of flow in said second measurement column;

said fluid supply means includes separate pumps for the reference and test fluids;

said heat exchanger means is positioned immediately upstream of said first and second measuring columns.

7. The device as claimed in claim 6, wherein;

each of said first and second measuring columns has on an upstream end an open beaker-type chamber with a cross-section to constitute a stabilizing chamber for a respective level of the fluid in said first and second measuring columns in relation to the pulses of the respective pumps.

8. The device as claimed in claim 6, wherein:

said exchanger means includes a chamber which has a substantial cross-section filled by exchanger fluid at a regular temperature to cause the reference and test fluids at a temperature different from each other to be equalized, said chamber including ducts which form part of said fluid supply means.

9. The device as claimed in claim 8, wherein:

said pump of said fluid supply means for the reference fluid is installed downstream of the filter, and upstream of the heat exchanger, said filter being an activated carbon type.

10. A device in accordance with claim 1, further comprising:

first detection means connected to said first measuring column and for measuring a speed of the bubbles in said first column;

second detection means connected to said second measuring column and for measuring a speed of the bubbles in said second column.

11. A device for measuring a surfactant substance, the device comprising:

a first measuring column for containing a reference fluid;

a second measuring column for containing a test fluid;

a first bubble means connected to said first measuring column and for generating bubbles in said first column;

a second bubble means connected to said second measuring column and for generating bubbles in said second column;

flow stabilization means connected to said first and second measuring columns to create separate flows through said first and second measuring columns and to maintain the flows in said first and second measuring columns substantially constant and similar, said flows being substantially opposite to a buoyancy direction of the bubbles;

a first and second sensor positioned spaced from each other on said first measuring column;

a first and second sensor positioned spaced from each other on said second measuring column, said first sensors on said first and second measuring columns having substantially similar positions on respective said first and second measuring columns, said second sensors on said first and second measuring columns having substantially similar positions on respective said first and second measuring columns.

12. The device as claimed in claim 11, wherein each sensor is a single or multiple optical sensor, and is designed in order to ensure that substantially all of the cross-section of one of the first and second measuring columns is checked.

13. The device as claimed in claim 11, wherein:

said first and second bubble means are formed from two sections of a single capillary tube, divided so as to be equal.

14. The device as claimed in claim 11, further comprising:

automatic solenoid valve means for discharging fluid from the first and second measurement columns, and for closing the first and second bubble means each time operation of the device is interrupted.

15. The device as claimed in claim 11, further comprising:

computerization means to determine a mean of a time of passage of a last n bubbles generated, n being set at will.

16. A device for measuring a surfactant substance in a test fluid, the device comprising:

a first measuring column for containing a reference fluid;

a second measuring column for containing a test fluid, the test fluid being separate from and different than the reference fluid;

a first bubble means connected to said first measuring column and for generating bubbles which flow within said first measuring column and through the reference fluid in said first measuring column from a bottom to a top of said first measuring column;

a second bubble means connected to said second measuring column and for generating bubbles in which flow within said second measuring column and through the test fluid in said second measuring column from a bottom to a top of said second measuring column;

first detection means connected to said first measuring column and for measuring a speed of the bubbles in said first column as the bubbles flow through the reference fluid;

second detection means connected to said second measuring column and for measuring a speed of the bubbles in said second column as the bubbles flow through the test fluid.

17. A device in accordance with claim 16, further comprising:

means for supplying the reference fluid and the test fluid to said first and second measuring columns at substantially similar conditions.

18. A device in accordance with claim 16, wherein:

said first and second detection means also measure a difference between the speeds of the bubbles in said first and second columns.

19. A device in accordance with claim 16, further comprising:

control system means connected to said first and second detection means and for determining a concentration of the surfactant substances by a difference in speeds of the bubbles in the reference and test solutions.

20. A device for measuring a surfactant substance, the device comprising:

a first measuring column for containing a reference fluid;

a second measuring column for containing a test fluid;

a first bubble means connected to said first measuring column and for generating bubbles in said first column;

a second bubble means connected to said second measuring column and for generating bubbles in said second column;

first detection means connected to said first measuring column and for measuring a speed of the bubbles in said first column, said first detection means intending a first and second sensor positioned spaced from each other on said first measuring column;

second detection means connected to said second measuring column and for measuring a speed of the bubbles in said second column, said second detection means including a first and second sensor positioned spaced from each other on said second measuring column, said first sensors on said first and second measuring columns having substantially similar positions on respective said first and second measuring columns, said second sensors on said first and second measuring columns having substantially similar positions on respective said first and second measuring columns.

* * * * *